United States Patent
Reid, Jr. et al.

(10) Patent No.: US 9,168,178 B2
(45) Date of Patent: Oct. 27, 2015

(54) ENERGY-DELIVERY SYSTEM AND METHOD FOR CONTROLLING BLOOD LOSS FROM WOUNDS

(75) Inventors: William O. Reid, Jr., Longmont, CO (US); James E. Dunning, Lafayette, CO (US); Kaylen J. Haley, Westminster, CO (US); Gayle L. Argoudelis, Louisville, CO (US)

(73) Assignee: Covidien LP, Mansfield, MA (US)

( * ) Notice: Subject to any disclaimer, the term of this patent is extended or adjusted under 35 U.S.C. 154(b) by 546 days.

(21) Appl. No.: 13/477,260

(22) Filed: May 22, 2012

(65) Prior Publication Data

US 2013/0317407 A1  Nov. 28, 2013

(51) Int. Cl.
| | |
|---|---|
| A61F 13/00 | (2006.01) |
| A61B 18/14 | (2006.01) |
| A61B 18/18 | (2006.01) |
| A61M 35/00 | (2006.01) |
| A61B 18/00 | (2006.01) |
| A61B 18/08 | (2006.01) |

(Continued)

(52) U.S. Cl.
CPC ........... *A61F 13/00068* (2013.01); *A61B 18/14* (2013.01); *A61B 18/1815* (2013.01); *A61B 18/082* (2013.01); *A61B 18/1206* (2013.01); *A61B 2018/0063* (2013.01); *A61B 2018/00589* (2013.01); *A61B 2018/00821* (2013.01); *A61B 2018/144* (2013.01); *A61B 2018/162* (2013.01); *A61B 2018/1892* (2013.01); *A61M 35/00* (2013.01)

(58) Field of Classification Search
CPC .............. A61N 2005/0647; A61N 2005/0651; A61N 2005/0656; A61N 2005/0662; A61N 2/008; A61N 5/0601; A61N 5/0616; A61N 5/0618; A61N 5/0622; A61N 5/6833; A61N 2560/0412; A61N 5/02055; A61N 5/04085; A61K 45/06; A61K 31/155; A61K 31/416; A61K 31/05; A61K 31/135; A61K 31/195; A61K 31/353; A61K 31/355; A61K 31/4468; A61K 31/4985; A61K 31/519; A61K 31/5513; A61K 31/573; A61K 33/06
USPC .................. 602/42–54; 604/20, 22, 46; 601/2
See application file for complete search history.

(56) References Cited

U.S. PATENT DOCUMENTS

| | | |
|---|---|---|
| D223,367 S | 4/1972 | Kountz |
| D263,020 S | 2/1982 | Rau, III |
| D266,842 S | 11/1982 | Villers et al. |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Michael Brown

(57) ABSTRACT

An energy delivery system for controlling blood loss is provided. The system includes an energy-activated patch configured for placement on tissue. The patch includes an energy-delivering layer configured to deliver energy to the tissue. The system also includes an energy source in operative engagement with the energy-activated patch for energizing the energy-delivering layer.

17 Claims, 3 Drawing Sheets

(51) Int. Cl.
*A61B 18/12* (2006.01)
*A61B 18/16* (2006.01)

(56) References Cited

U.S. PATENT DOCUMENTS

| | | | |
|---|---|---|---|
| D278,306 S | 4/1985 | McIntosh | |
| D295,893 S | 5/1988 | Sharkany et al. | |
| D295,894 S | 5/1988 | Sharkany et al. | |
| 5,100,422 A | 3/1992 | Berguer et al. | |
| D354,218 S | 1/1995 | Van de Peer | |
| 5,643,596 A | 7/1997 | Pruss et al. | |
| D424,693 S | 5/2000 | Pruter | |
| D424,694 S | 5/2000 | Tetzlaff et al. | |
| D425,201 S | 5/2000 | Tetzlaff et al. | |
| 6,056,970 A | 5/2000 | Greenawalt et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,589,269 B2 | 7/2003 | Zhu et al. | |
| D487,039 S | 2/2004 | Webster et al. | |
| D496,997 S | 10/2004 | Dycus et al. | |
| D499,181 S | 11/2004 | Dycus et al. | |
| 6,908,448 B2 * | 6/2005 | Redding, Jr. | 604/22 |
| 7,029,466 B2 | 4/2006 | Altman | |
| D525,361 S | 7/2006 | Hushka | |
| 7,100,614 B2 | 9/2006 | Stevens et al. | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| 7,392,080 B2 | 6/2008 | Eppstein et al. | |
| D576,932 S | 9/2008 | Strehler | |
| 7,440,798 B2 * | 10/2008 | Redding, Jr. | 604/20 |
| 7,482,503 B2 | 1/2009 | Gregory et al. | |
| D594,736 S | 6/2009 | Esjunin | |
| D594,737 S | 6/2009 | Kelly et al. | |
| D606,203 S | 12/2009 | Husheer et al. | |
| 7,641,612 B1 | 1/2010 | McCall | |
| 7,662,151 B2 * | 2/2010 | Crompton et al. | 606/41 |
| D613,412 S | 4/2010 | DeCarlo | |
| D634,010 S | 3/2011 | DeCarlo | |
| 2005/0080465 A1 * | 4/2005 | Zelickson et al. | 607/88 |
| 2005/0137512 A1 | 6/2005 | Campbell et al. | |
| 2006/0009731 A1 | 1/2006 | Wu et al. | |
| 2008/0146984 A1 | 6/2008 | Campbell et al. | |
| 2010/0130912 A1 | 5/2010 | Berenson | |
| 2011/0034410 A1 | 2/2011 | McCarthy et al. | |
| 2011/0054577 A1 * | 3/2011 | Latham | 607/112 |
| 2012/0289757 A1 * | 11/2012 | Boyden et al. | 600/1 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 107 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO00/36985 | 6/2000 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.

(56) References Cited

OTHER PUBLICATIONS

U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.

C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.

(56) References Cited

OTHER PUBLICATIONS

Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics Figo World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.825.
Urologix, Inc.-Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.

(56) References Cited

OTHER PUBLICATIONS

Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.

(56) References Cited

OTHER PUBLICATIONS

European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
HyFin Chest Seal, www.narescue.com/HyFin_Chest_Seal-CN1BB57448570E.html?BC=3C7457EA9AFA, printed Aug. 22, 2011.

\* cited by examiner

ENERGY-DELIVERY SYSTEM AND METHOD FOR CONTROLLING BLOOD LOSS FROM WOUNDS

BACKGROUND

1. Technical Field

The present disclosure relates to controlling blood loss, and, in particular, to an energy delivery system and method for the sealing and/or coagulation of a wound for controlling and stopping blood loss.

2. Description of Related Art

In situations involving traumatic wounds, controlling bleeding within the first hour or "golden hour" leads to improved survival rates. Typical methods for control of blood loss include tourniquets and compression bandages. Additionally, in recent years, the military has introduced the use of coagulants, such as zeolite, that promote clotting of wounds.

Tourniquets and other devices may cause collateral damage to surrounding tissue and fail to actively coagulate the wound. Further, tourniquets are not always feasible for particular types of wounds, such as chest wounds. A system that can effectively stop the loss of blood from injuries caused by accidents, warfare and natural disasters would be a vital tool in the stabilization and triage of patients.

SUMMARY

The present disclosure relates to blood loss control, and, in particular, to energy delivery systems and methods for the sealing and/or coagulation of a wound.

According to an aspect of the present disclosure, an energy delivery system for controlling blood loss is provided. The system includes an energy-activated patch configured for placement on tissue. The patch includes an energy-delivering layer configured to deliver energy to the tissue. The system further includes an energy source in operative engagement with the energy-activated patch for energizing the energy-delivering layer. The patch further includes an energy-activated gel layer in proximity to the energy-delivering layer. The energy-activated gel layer includes a coagulant. The energy-activated gel layer includes a medicament.

The energy-activated patch further includes a tissue support layer in proximity to the energy-activated gel layer. The tissue support layer includes a bio-material.

The energy-activated patch further includes a barrier layer in proximity to the energy-delivering layer. The barrier layer is disposed between the energy-activated gel layer and the energy-delivering layer. The barrier layer includes an occlusive dressing.

The energy-delivering layer includes a microstrip antenna or electrodes. The energy-delivery layer can include a microwave mesh patch or a grid of active and return RF electrodes. The energy source is portable and can be a microwave generator or a RF generator. The energy delivery system further includes a thermocouple sensor operatively engaged to the patch.

In another aspect of the present disclosure, an energy-activated patch configured for placement on tissue includes an energy-activated gel layer; and an energy-delivering layer in proximity to the gel layer. The gel layer includes a heat-activated coagulant. The patch further includes a tissue support layer in proximity to the gel layer. The tissue support layer includes a bio-material.

In a further aspect of the present disclosure, there is provided a method for controlling blood loss. The method includes the steps of applying an energy-activated patch and an energy activated gel to a wound site, and supplying energy to the energy-activated patch to create a seal at the wound site by the energy activated gel. The method also includes the step of applying an occlusive dressing to the wound site after applying the gel to the wound site. The method also includes applying an occlusive dressing to the wound site prior to applying the energy-activated patch to the wound site.

BRIEF DESCRIPTION OF THE DRAWINGS

These and other advantage will become more apparent from the following detailed description of the various embodiments of the present disclosure with reference to the drawings wherein.

DETAILED DESCRIPTION

Figure 1:
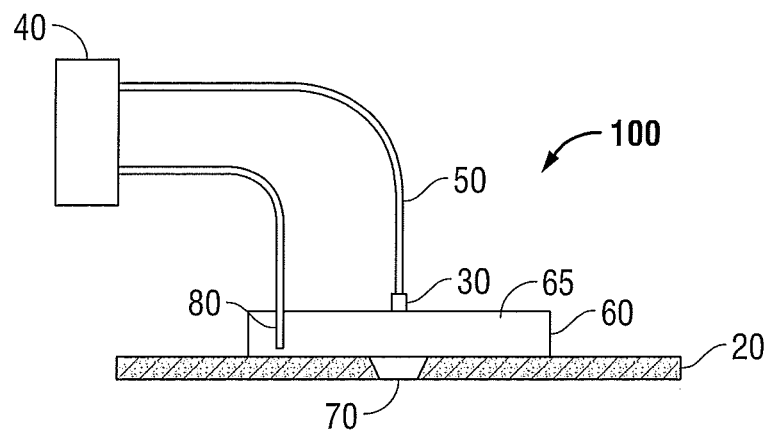
FIG. 1 is a schematic diagram of an exemplary system for supplying energy to an energy-activated patch for delivery to a wound site in accordance with a first embodiment of the present disclosure.

Embodiments of the presently disclosed system and method for controlling blood loss will now be described in detail with reference to the drawings in which like reference numerals designate identical or corresponding elements in each of the several views. Even though features may be described herein with respect to a particular embodiment, it is understood that the various features described herein can be incorporated within other embodiments.

In one embodiment, an energy delivery system for controlling blood loss is provided. The system includes an energy-activated patch configured for placement on tissue. The patch includes an energy-delivering layer configured to deliver energy to the tissue. The system further includes an energy source in operative engagement with the energy-activated patch for energizing the energy-delivering layer. The patch further includes an energy-activated gel layer in proximity to the energy-delivering layer. The energy-activated gel layer includes a coagulant. The energy-activated gel layer includes a medicament.

The energy-activated patch further includes a tissue support layer in proximity to the energy-activated gel layer. The tissue support layer includes a bio-material.

The energy-activated patch further includes a barrier layer in proximity to the energy-delivering layer. The barrier layer is disposed between the energy-activated gel layer and the energy-delivering layer. The barrier layer includes an occlusive dressing.

The energy-delivering layer includes a microstrip antenna or electrodes. The energy-delivering layer can include a microwave mesh patch or a grid of active and return RF electrodes. The energy source is portable and can be a microwave generator or an RF generator. The energy delivery system further includes a thermocouple sensor operatively engaged to the patch.

In another embodiment, an energy-activated patch configured for placement on tissue includes an energy-activated gel layer; and an energy-delivering layer in proximity to the gel layer. The gel layer includes a heat-activated coagulant. The patch further includes a tissue support layer in proximity to the gel layer. The tissue support layer includes a bio-material.

In a further embodiment, there is provided a method for controlling blood loss. The method includes the steps of applying an energy-activated patch and an energy activated gel to a wound site, and supplying energy to the energy-activated patch to create a seal at the wound site by the energy activated gel. The method also includes the step of applying an occlusive dressing to the wound site after applying the gel to the wound site. The method also includes applying an occlusive dressing to the wound site prior to applying the energy-activated patch to the wound site.

Reference is first made to FIG. 1, which shows an energy delivery system 100 in contact with the surface of a patient's skin 20, the energy delivery system 100 includes a terminal 30 connected to an energy source 40, such as an RF or microwave generator, via a wire or cable 50 and a patch 60. The patch 60 has an energy-delivering layer 65 for delivering energy to the wound 70 when the energy source 40 is activated. The energy promotes active coagulation of the blood thus sealing the wound 70 and stopping blood loss. One or more thermocouple sensors 80 incorporated into the patch 60 monitor the skin 20 and/or the temperature of the patch 60 for safety and treatment monitoring.

The energy-delivering layer 65 may include coagulants and/or hemostatic materials which are activated by heat. Therefore, as the energy delivered to the energy-delivering layer 65 heats the layer 65, the coagulants and/or hemostatic materials which are included with the layer 65 are activated. The activated coagulants and/or hemostatic materials exhibit coagulation and/or hemostatic properties which stop or minimize blood loss at the wound 70.

The energy source 40 may be a small handheld device suitable for use, for example, by military medics. In an alternative embodiment, the energy source 40 may be portable and configured for connecting to an electrical outlet of a vehicle, such as an ambulance. In particular, the energy source can by any type of energy source capable of delivering energy of sufficient amount for activating the coagulants and/or hemostatic materials within the energy-delivering layer 65. For example, the energy source can be of the type capable of delivering microwave, RF, or other forms of energy.

The energy-delivering layer 65 does not necessarily need to include any coagulants and/or hemostatic materials. For example, the energy-delivering layer can be manufactured from materials capable of delivering energy in the form of heat to the wound 70 for stopping blood loss by cauterization or charring of the tissue. In such an embodiment, the thermocouple 80 can be used to monitor the temperature of the energy-delivering layer 65 to prevent excessive burning of the tissue.

Figure 2:
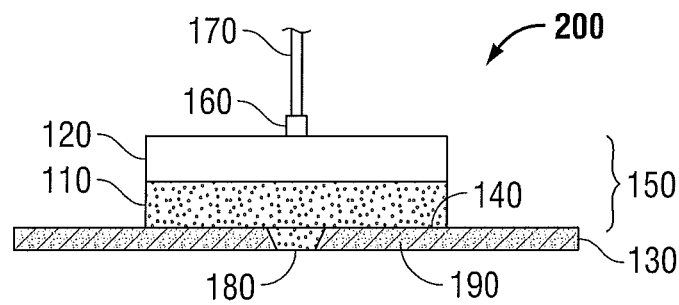
FIG. 2 is a cross-sectional view of an energy-activated patch in accordance with a second embodiment of the present disclosure.

In accordance with another embodiment with reference to FIG. 2, an energy delivery system 200 includes an energy-activated patch 150 having a gel 110 and an energy-delivering layer 120. The gel 110 is used to facilitate adhesion of the energy-delivering layer 120 to the skin 190. A terminal 160 is provided on the patch 150 for connecting to an energy source (not shown) via a wire or cable 170.

The tissue-contacting surface 140 of the gel 110 may also have coagulants and/or hemostatic materials that promote coagulation of the blood. The coagulants and/or hemostatic materials may promote coagulation upon making contact with blood at the wound site 180 or upon being heated by the energy delivered by the energy source. The gel 110 can serve as a spacer/medium between the tissue or skin 190 to be heated and the energy-delivering layer 120. As a spacer/medium, the gel 110 increases the surface area of tissue 190 exposed to the radiation being delivered by the energy-delivering layer 120.

In embodiments described herein, depending on the gel or other gel-like substance used (collectively referred to herein as gels), the gel can coagulate upon heating or upon making contact with blood. In embodiments described herein, the gel includes one or more drugs therein which are delivered upon activation of the gel or upon application of the patch 150 on the wound 180. The drugs can be, for example, a pain reliever, anesthetic, etc.

Additionally, in embodiments described herein, the gel can be a hydrogel of the type manufactured by Covidien Ludlow. Further, in embodiments described herein, the gel can also be bovine serum albumin powder (BSA) dissolved in water. In other embodiments, the gel may be adhesive, viscous, liquid, solid and/or flexible.

Figure 3:
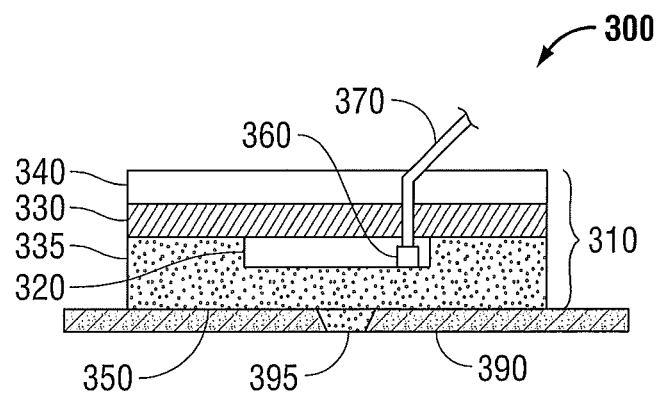
FIG. 3 is a cross-sectional view of an energy-activated patch having a microstrip antenna embedded within gel in accordance with a third embodiment of the present disclosure.

In reference to FIG. 3, there is shown another embodiment of an energy delivery system 300. The system 300 includes a patch 310 having an energy-delivering layer 335 configured to contact the skin 390. The energy-delivering layer 335 can include a microstrip antenna 320. The microstrip antenna 320 is placed on a dielectric substrate 330 which in turn is placed on a ground plane layer 340. The radiation pattern of the microstrip antenna 320 covers a wide area. The microstrip antenna 320 can include a microwave mesh patch. Other antenna structures can be utilized in place or in addition to the microstrip antenna 320.

The energy-delivering layer 335 includes an adhesion material 350, which can include a gel. The adhesion material 350 covers the microstrip antenna 320 and the dielectric substrate 330. The adhesion material 350 can include material which prevents the attenuation of the energy delivered to the tissue, and/or material which increases the amount of surface area of the skin exposed to the microwave radiation. The energy is delivered from an energy source (not shown) coupled via a wire or cable 370 to a terminal 360. The terminal is fixed or connected to the microstrip antenna 320.

In a further embodiment of the present disclosure, energy may be delivered to the patches described herein by various modalities including, but not limited to, RF and microwave. If microwave energy is used, then the microstrip antenna shown by FIG. 3 can be, for example, a microwave mesh patch. The microwave mesh patch can include shielding capable of directing energy generated by the energy source towards the wound site. If RF energy is used then the patch can include or be replaced with material having a grid of active and return RF electrodes that generate heat in the gel. Resistive heating is also contemplated.

Figure 4:
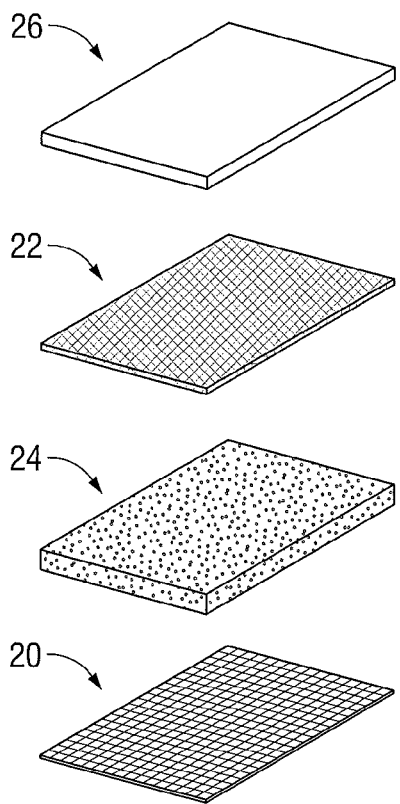
FIG. 4. is an exploded view of an energy-activated patch with a microwave mesh patch in accordance with a fourth embodiment of the present disclosure.
Figure 5:
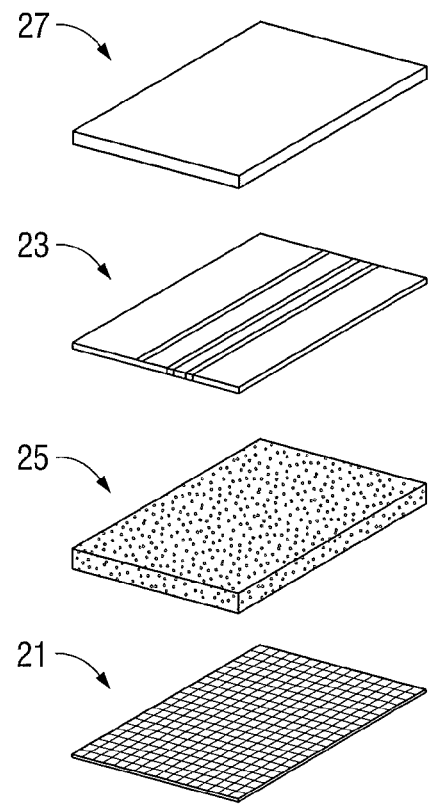
FIG. 5 is an exploded view of a patch having an energy-delivering layer which includes a grid of RF active and return electrodes in accordance with a fifth embodiment of the present disclosure.

With reference to FIGS. 4 and 5, there are shown exploded views of a patch having several layers, including a microwave mesh patch in accordance with a fifth embodiment of the present disclosure and a layer having RF active and return electrodes in accordance with a sixth embodiment of the present disclosure. Both embodiments of the patch include a tissue support layer 20, 21 adjacent to, or embedded within, a gel layer 24, 25 to provide structural support to the wound area. The support layer 20, 21 may be a scaffold made of a bio-material, such that the support layer 20, 21 is absorbed by the tissue over time.

In embodiments, the support layer 20, 21 and/or the gel layer 24, 25 include medicaments, coagulants, etc. The patch shown by FIG. 4 includes an energy-delivering layer 22 which includes a grid of RF active and return electrodes. The patch shown by FIG. 5 includes an energy-delivering layer 23 having a microwave mesh patch. A backing 26, 27 can be provided, which lies adjacent to the energy-delivering layers, 22, 23.

A terminal (not shown) is provided to each patch for delivering energy from an energy source to the energy-delivering layers 22, 23. The terminal can be connected directly to the layers 22, 23. As described herein with respect to the other embodiments, energy is delivered to the patches shown by FIGS. 4 and 5 by the energy source after the patch has been placed over a wound site.

The energy activates the gel layer 24, 25 for causing the gel layer 24, 25 to promote coagulation as described herein for the other embodiments. For example, coagulants and/or hemostatic materials within the gel layer 24, 25 promote coagulation upon being heated by the energy delivered by the energy source. The coagulants and/or hemostatic materials may also be selected for promoting coagulation without being heated.

Figure 6:
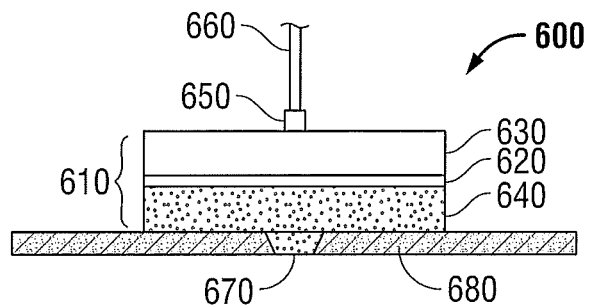
FIG. 6 is a cross-sectional view of a patch having an energy-delivering layer which includes a microwave mesh patch in accordance with a sixth embodiment of the present disclosure.

In reference to FIG. 6 there is shown another embodiment of an energy delivery system 600 according to the present disclosure. The system 600 includes a patch 610 having a barrier layer 620 disposed between an energy-delivering layer 630 and a gel layer 640 to prevent the gel 640 from sticking to the energy-delivering layer 630. The barrier layer 620 may be made of any material that prevents the energy-delivering layer 630 from making direct contact with the gel layer 630. The material can be an occlusive dressing. The material may also be selected to have a low radiation deflection property to prevent the deflection of the energy delivered to the gel layer 630 through the barrier layer 620. A material known to have a low deflection property that may be used for the barrier layer 620 is Tykek® spunbonded olefin. In embodiments, the barrier layer 620 and the gel 640 may be an occlusive dressing, such as HyFin® chest seal.

In embodiments described herein, the thickness of the various components and layers shown by the Figures are for illustrative purposes only and do not necessarily indicate desired proportions of these components and layers.

Figure 7:
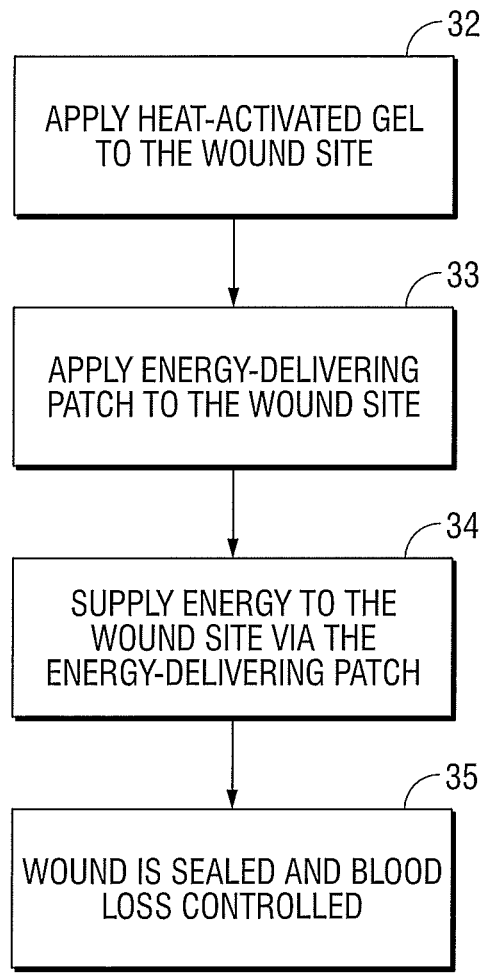
FIG. 7 is a flow chart illustrating a method for controlling blood loss from wounds using an energy-activated patch in accordance with the present disclosure.

FIG. 7 illustrates a flow chart showing a method according to the present disclosure. The method includes applying gel to a wound site, step 32. The gel can be applied with an energy-activated patch, as the patches described herein, or prior to placing the patches described herein on the wound site. It is also contemplated that the gel is applied prior to applying the patch and that the patch also include a gel layer. A barrier layer can be placed over the gel applied to the wound site.

After the gel is applied in step 32, the energy-activated patch is applied to the wound site, step 33. Energy is then supplied to the wound site via the energy-activated patch, step 34. Once the patch is activated it promotes coagulation for controlling blood loss and sealing the wound, step 35.

In embodiments, the energy is delivered directly to the wound site using an energy-delivery system as shown, for example, by FIG. 1, or by FIGS. 3-6 with the gel layer removed.

The energy delivery systems described herein can be applied in military applications. For example, energy-activated patches could be issued to military personnel prior to deployment into a battle situation. A portable, handheld energy source can be used to energize the patches if necessary on the battlefield. The energy source can also be issue to military personnel or to military medics.

The energy delivery systems can also be used in non-military applications, such as, for example, paramedics or hospitals. The systems can be provided to ambulance companies for usage in emergency situations where controlling bleeding is paramount.

Features of the various embodiments of the energy-delivery systems and patches described herein in accordance with the present disclosure may be incorporated into one or more other embodiments. Further, embodiments can be designed for different functional frequencies. Additionally, various sizes and shapes can be designed for different treatment modalities and types of wounds. Possible shapes can be rectangular, circular, square, triangular and amorphous. Flexible materials can also be used for the various components described herein to allow for adequate contact and shaping of the patch. The various components can also be made of bio-materials which may be absorbed within the wound site after a time period.

Although the illustrative embodiments of the present invention have been described herein with reference to the accompanying drawings, it is to be understood that the invention is not limited to those precise embodiments, and that various other changes and modifications may be affected therein by one having ordinary skill in the art without departing from the scope or spirit of the invention. Accordingly, various modifications and variations can be made without departing from the spirit or scope of the invention as set forth in the following claims both literally and in equivalents recognized in law.

What is claimed:

1. An energy delivery system for delivering energy to a wound and controlling blood loss by promoting coagulation of the blood thus sealing the wound, the system comprising:
    an energy-activated patch configured for placement on tissue in proximity to the wound, the patch includes an energy-delivering layer configured to deliver energy to the wound to promote coagulation of the blood thus sealing the wound, the energy-delivering layer including a microstrip antenna; and
    an energy source in operative engagement with the energy-activated patch for energizing the energy-delivering layer.

2. The energy delivery system according to claim 1, wherein the patch further includes an energy-activated gel layer in proximity to the energy-delivering layer.

3. The energy delivery system according to claim 2, where the energy-activated gel layer includes a coagulant.

4. The energy delivery system according to claim 3, wherein the energy-activated patch further includes a tissue support layer in proximity to the energy-activated gel layer.

5. The energy delivery system according to claim 4, wherein the tissue support layer includes a bio-material.

6. The energy delivery system according to claim 3, wherein the energy-activated patch further includes a barrier layer disposed between the energy-activated gel layer and the energy-delivering layer.

7. The energy delivery system according to claim 6, wherein the barrier layer includes an occlusive dressing.

8. The energy delivery system according to claim 2, wherein the energy-activated gel layer includes a medicament.

9. The energy delivery system according to claim 1, wherein the energy-activated patch further includes a barrier layer in proximity to the energy-delivering layer.

10. The energy delivery system according to claim 1, wherein the microstrip antenna includes a microwave mesh patch.

11. The energy delivery system according to claim 1, wherein the energy source is portable.

12. The energy delivery system according to claim 1, wherein the energy source is at least one of a microwave generator and an RF generator.

13. The energy delivery system according to claim 1, further including a thermocouple sensor operatively engaged to the patch.

14. An energy delivery system for controlling blood loss, the system comprising:
- an energy-activated patch configured for placement on tissue, the patch includes an energy-delivering layer configured to deliver energy to the tissue; and
- an energy source in operative engagement with the energy-activated patch for energizing the energy-delivering layer, wherein the energy-delivering layer includes a microstrip antenna.

15. The energy delivery system according to claim 14, wherein the microstrip antenna includes a microwave mesh patch.

16. An energy delivery system for controlling blood loss, the system comprising:
- an energy-activated patch configured for placement on tissue, the patch includes an energy-delivering layer configured to deliver energy to the tissue; and
- an energy source in operative engagement with the energy-activated patch for energizing the energy-delivering layer, wherein the energy-delivering layer includes a grid of active and return RF electrodes.

17. An energy delivery system for delivering energy to a wound and controlling blood loss by promoting coagulation of the blood thus sealing the wound, the system comprising:
- an energy-activated patch configured for placement on tissue in proximity to the wound, the patch includes an energy-delivering layer configured to deliver energy to the wound to promote coagulation of the blood thus sealing the wound, the energy-delivering layer including a grid of active and return RF electrodes; and
- an energy source in operative engagement with the energy-activated patch for energizing the energy-delivering layer.

* * * * *